United States Patent [19]

Bates

[11] Patent Number: 5,386,825
[45] Date of Patent: Feb. 7, 1995

[54] RESPIRATORY BREATHING FILTER APPARATUS AND METHOD

[76] Inventor: Charles W. Bates, 450 E. 126th St., Los Angeles, Calif. 90061

[21] Appl. No.: 63,776

[22] Filed: May 20, 1993

[51] Int. Cl.⁶ ............................................. A62B 7/10
[52] U.S. Cl. ...................... 128/205.27; 128/205.28; 128/205.29; 128/204.13; 128/206.15; 128/206.29
[58] Field of Search ............ 128/205.27, 205.29, 128/206.29, 201.11, 204.13, 203.23, 207.14, 205.28, 206.15

[56] References Cited

U.S. PATENT DOCUMENTS

| | | | |
|---|---|---|---|
| 413,100 | 10/1889 | Smith | 128/203.23 |
| 589,712 | 9/1897 | Fouquier | 128/202.16 |
| 603,021 | 4/1898 | Dight | 128/201.13 |
| 657,866 | 9/1900 | Fike | 128/204.13 |
| 712,304 | 10/1902 | Jacobs et al. | 128/204.13 |
| 893,213 | 7/1908 | Whiteway | 128/203.23 |
| 971,214 | 11/1869 | Montgomery | 128/203.23 |
| 1,043,689 | 11/1912 | Göttlieb | 128/204.13 |
| 1,134,993 | 4/1915 | Bye | 128/202.17 |
| 2,642,063 | 6/1953 | Brown | 128/203.15 |
| 3,027,897 | 4/1962 | Carofiglio | 128/203.23 |
| 3,747,598 | 7/1973 | Cowans | 128/201.13 |
| 3,774,601 | 11/1973 | Langone | 128/206.11 |
| 4,098,270 | 7/1978 | Dolby | 128/206.29 |
| 4,201,206 | 5/1980 | Kuehn et al. | 128/201.13 |
| 4,231,364 | 11/1980 | Speshyock | 128/207.14 |
| 4,262,666 | 4/1981 | Nelson | 128/204.13 |
| 4,478,215 | 10/1984 | Hanlon | 128/207.14 |
| 5,207,221 | 5/1993 | Stulbach | 128/206.29 |

Primary Examiner—Edgar S. Burr
Assistant Examiner—Aaron J. Lewis

[57] ABSTRACT

An advanced and versatile method for a RESPIRATORY BREATHING FILTER APPARATUS having an outer body that conforms to the natural formation of the human mouth and is engaged by the teeth without the use of hands. Primarily designed for use by users with respiratory ailments, (i.e., asthma, emphysema, allergies related to respiratory problems) the apparatus can be used by users engaged in aerobic activities with safety and fewer body restrictions. The apparatus has an outer body and five removable component parts. The outer body contains an outer or frontal filter for removal of coarse foreign airborne or macro-particles in an incoming airstream. The second of the filters, separate from the outer filter in the outer body, is designed to remove smaller or micro-particles from the incoming airstream. This second filter is easily removed, which is a tremendous advantage from previously presented methods and systems. A medicament with minimal dosage is evaporatively added to the incoming airstream and provides aided relief to the user having respiratory tract ailments. A removable retaining ring maintains the second filter and medicament in place during use. Two one-way valves open during exhalation and close during inhalation. Method of use is also disclosed.

3 Claims, 2 Drawing Sheets

RESPIRATORY BREATHING FILTER APPARATUS AND METHOD

BACKGROUND OF INVENTION

1. Field of the Invention

The RESPIRATORY BREATHING FILTER APPARATUS relates to filter devices worn in the mouth and provides versatile filtering capabilities due to the removal and/or addition of the component parts.

2. Brief Description of the Prior Art

Speshyock teaches a breathing device received within the mouth of the user which filters and enhances inhaled air by the addition of medicament. Note the shield (32), and that the mouth is kept open (FIG. 1). Montgomery teaches that a respiratory filter can be worn on a chain around a user's neck when not needed (FIG. 5). Jacobs et al., Langone, Nelson, and Hanlon all teach filters that are received within a user's mouth. Brown teaches a valved inhalation filter. Smith, Bye, Carofiglio, and Fouquier all teach respiratory filters with medicament inhaling means. The remaining references are all directed to mouth- or nose-inserted respiratory filters.

Respiratory breathing filters have taken several forms, varying from gas masks with sophisticated filtering techniques used by military and para-military personnel to filtering and breathing apparatus used by persons involved with occupations and activities in which harmful or contaminated gas or vapors were present, such as fumigation and painting occupations. The filtering devices used vary from a gauze or similar porous material to carbon or charcoal filtering to more sophisticated filtering, such as with nerve gases used in warfare. In each instance mentioned, the user's respiratory health condition was of average or good condition. The present Respiratory Breathing Filter Apparatus aids the individual as a preventative measure against the suffering of asthma attacks, emphysema and respiratory diseases related to allergies or polluted air. Respiratory disease is ranked the number six leading cause of death in the United States. With increased pollution and airborne allergens, respiratory ailments are ever increasing. From 1979 to 1987, the number of deaths from asthma nearly doubled. The National Heart, Lung and Blood Institute determined that the reasons for the increased number of incidents of respiratory ailments are due to the lack of immediate access to a doctor or hospital for care, lack of education, and undertreatment.

It is a well-known fact that allergies will trigger asthma. And in most cases the treatment involves the use of inhalers with corticosteroid sprays which reverses bronchial inflammation. Another drug used to prevent inflammation is "INTAL," cromolyn sodium. Other forms are bronchodilators, which can be in tablet form or used in inhalers or "nebulizers," which is a home aerosol machine to deliver higher doses of bronchodilator. With all this chemical inducement of various medication, the best-known remedy is home preventive therapy, doctors say. In the July 1, 1990, issue of the *Journal of Pediatrics*, Dr. Warren Richards concluded that many asthmatic children seen in the Children's Hospital emergency room (Los Angeles) are there because their asthma therapy was inadequate or nonexistent. This indicates a more active role or home therapy must be implemented. Dr. Albert Sheffer, clinical professor of medicine at Harvard Medical School and head of a federal panel advising doctors on how to treat asthma, said, "It's not whether you're an allergist or a pulmonary doctor. It's whether you take care of asthma. So it doesn't make any difference what the specialty is." Once again there is an emphasis on the care and prevention of asthma. There are an estimated 9.7 million asthmatics in the United States, and 3 million of them are under 18 years of age. From 1970 to 1985 the incidence of asthma increased 22 percent among Blacks. Males are twice as likely to be hospitalized for asthma as females. Asthma is a growing problem and requires a controlled or preventive solution. This invention of the Respiratory Breathing Filter Apparatus addresses itself to the problem of respiratory diseases as a preventive measure against asthma and respiratory inflammation brought on by airborne particles. At present, there are no known inventions related to respiratory breathing filters for the prevention of respiratory problems.

OBJECTS OF THE INVENTION

It is, therefore, one of the primary objects of the present invention to provide a respiratory breathing filter which is capable of removing both large-sized particles in an incoming airstream and for also removing smaller airborne particles and like particles from the airstream in order to clear the air for a user.

It is a further object of the present invention to provide a respiratory breathing filter of the type stated which utilizes a pair of spaced-apart filters. The forward filter is of a reusable porous material for removal of large airborne particles; and a second filter is for removal of smaller particles.

It is another object of the present invention to provide a respiratory breathing filter of the type stated in which a medicament is embedded in a sterile screen to be administered to the respiratory tract during inhalation to aid the user having respiratory ailment(s). The incoming air enters through one path; the exhaled air exits three separate paths to remove carbon dioxide from the respiratory tract of the user.

It is another object to provide a retaining ring. The retaining ring holds the second filter and medicament on the sterile screen in position during use. This retaining ring is removable.

It is another object to provide two one-way valves to increase the exhaled air flow. There are two removable one-way valves which will allow exhaled air to exit and prevent increased carbon dioxide levels. During inhalation the two one-way valves are closed and direct the air flow through the second filter in the interior of the apparatus.

It is another object of the present invention to provide a respiratory breathing filter which offers a mouthpiece as part of its outer body shape and size to conform to the natural contours of the human mouth.

It is an object of the present invention to offer versatile design which enables the user to increase air intake or flow by removing or altering the interior parts. The user will have the option to increase air flow on clear days, increase air filtration on smoggy days, and/or provide medicament to an already cleaned air flow.

It is further the object of the present invention to provide a shield for the teeth of the user by offering a cradle that surrounds the user's teeth similar to a boxer's or football player's mouthpiece.

It is another object of the present invention to provide a method or means of varying the air flow as an attempt to exercise the lungs of the user and to enhance deep breathing.

It is further the object to provide a means of moisturization of environmentally dry air (i.e., desert air). The outer filter that extends across the front of the mouthpiece can be used as a simple air conditioner by applying a small amount of liquid (i.e., water, juices or the like) to the filter, which will cool and moisten already dry airstream.

With the above and other objects in view, my intention resides in the novel features of form, construction, arrangement and combination of parts presently described and pointed out in the claims.

BRIEF SUMMARY OF THE INVENTION

The Respiratory Breathing Filter Apparatus is adapted to be engaged by the lips and teeth of a user in order to enable inhalations of air through the filters and into the lungs and through the mouth of the user. During exhalation, said apparatus increases air flow and reduces carbon dioxide retention by the use of two one-way valves. The Respiratory Breathing Filter Apparatus is highly effective for use by people without respiratory ailments and who engage in aerobic activities, such as sports activities, walking, dancing and the like, to breathe cleaner air. The Respiratory Breathing Filter Apparatus is highly effective for use by individuals suffering from respiratory tract disease since the apparatus is designed to cleanse the air and, moreover, to apply a medicament to the incoming airstream for application to the respiratory tract of the user.

The Respiratory Breathing Filter Apparatus is comprised of an arcuate outer body in a shape similar to a slice of an orange. The apparatus is comprised of an outer or first filter made of reusable porous material designed to remove coarse particles which may be entrained in an incoming airstream. An interior or second filter, separate from the first filter, is located within the body for removing any smaller particles, such as unwanted smog particulates, smoke and other small airborne particles which are entrained in the incoming airstream.

The housing of the Respiratory Breathing Filter Apparatus of the present invention may be constructed of an approved durable plastic. The housing may be provided with eyelets for supporting a neck strap or like retaining device in order to allow the apparatus to be suspended from the neck of the user while not in use. Due to the size and shape of the inventions, it is not readily visible, which could preclude any unnecessary annoying poking-of-fun by other children. There are other advantages to this invention which may be more clearly apparent from a consideration of design or form in which it may be embodied. While the invention has been described in general terms, the above description will set forth at least one specific form in which the invention may be embodied. However, it is to be understood that the following detailed description only set forth one preferred embodiment of the present invention and is therefore not to be taken in a limiting sense.

The apparatus provides versatility by allowing the user to include all or exclude some or all of the interior component parts. This procedure would vary the flow and/or filtration method. As an example, a hiker may desire the mountain air but would like to remove the dirt and pollen from the inhaled air. By removing the valve and/or second filter, the user can increase incoming air flow and/or decrease filtering of said incoming air.

BRIEF DESCRIPTION OF THE DRAWINGS

Figure 1:
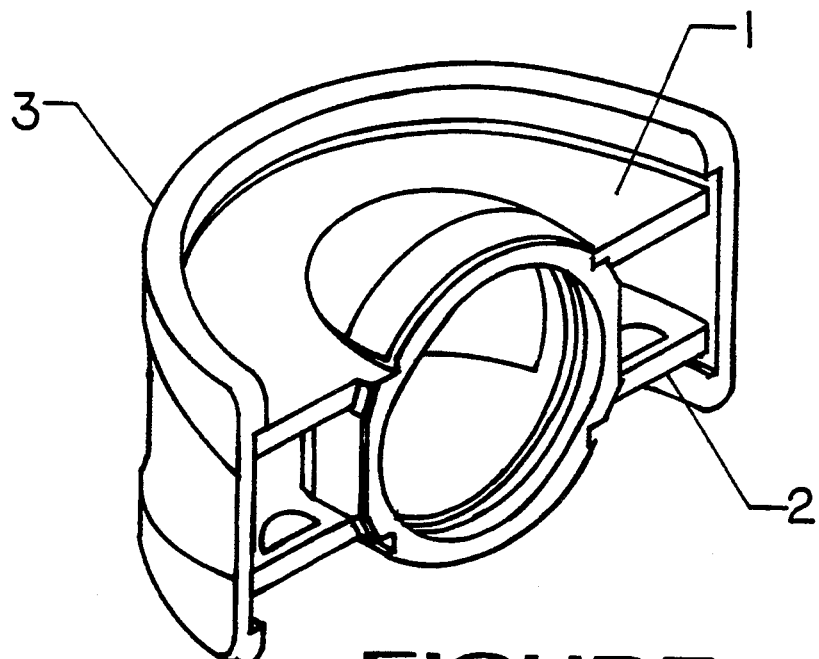
Figure 2:
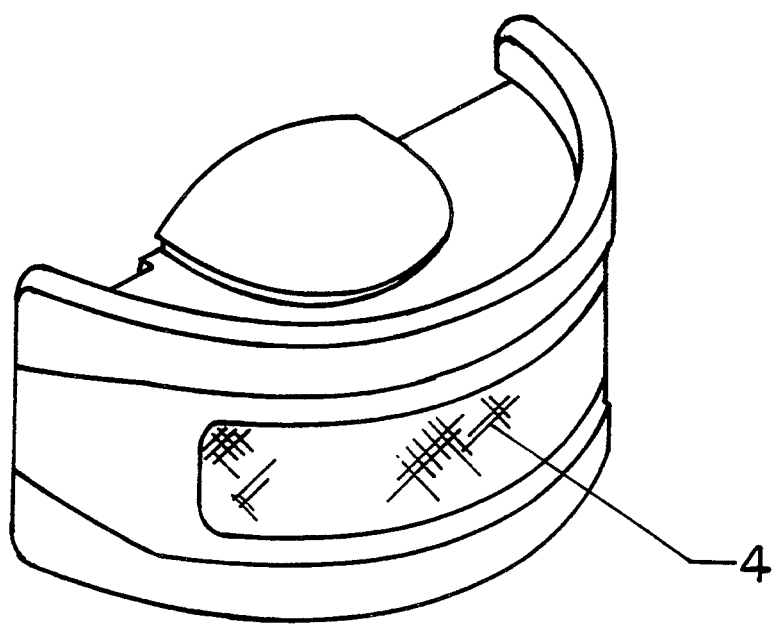
Figure 3:
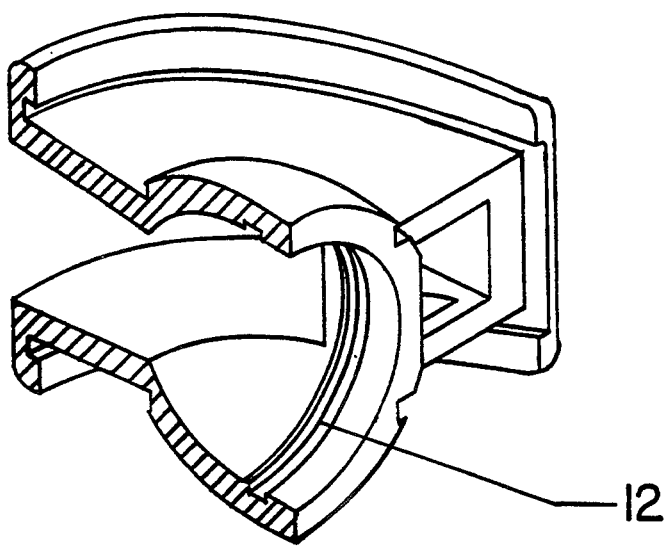
Figure 4:
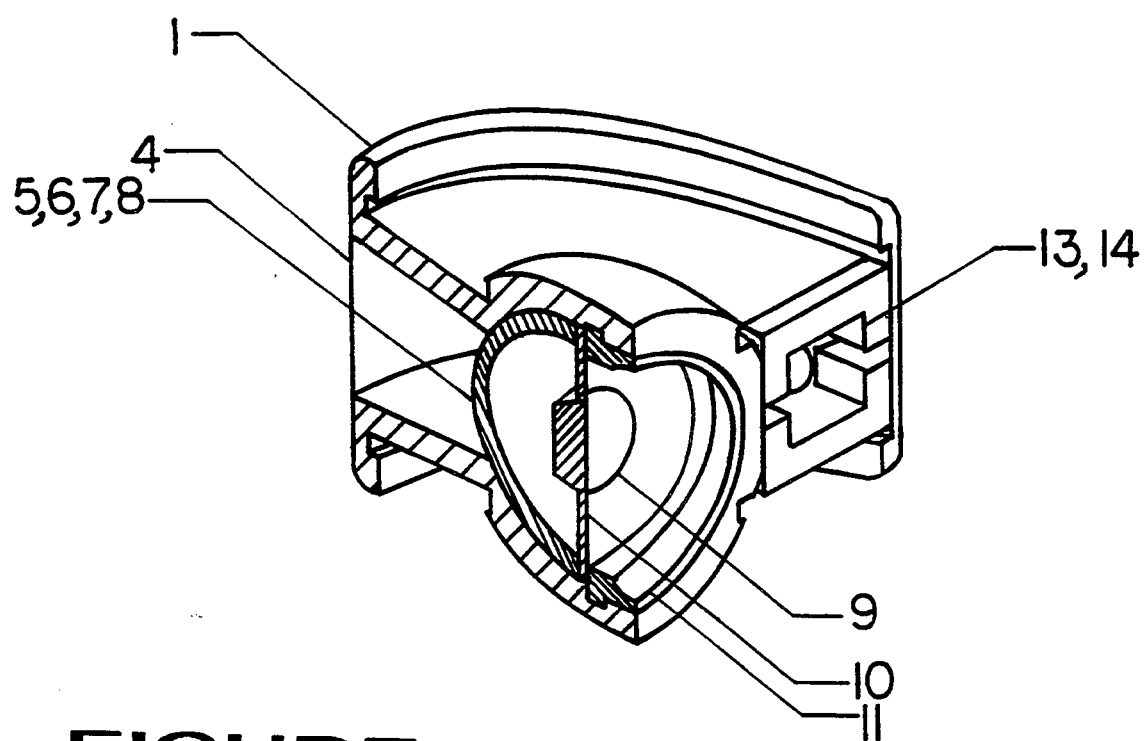

Having thus described in general terms, reference will now be made to the accompanying drawings in which:

FIG. 1 is a rear view of the Respiratory Breathing Filter Apparatus outer body;

FIG. 2 is the frontal view of the Respiratory Breathing Filter Apparatus of FIG. 1;

FIG. 3 is an isometric view of the Respiratory Breathing Filter Apparatus of FIG. 1;

FIG. 4 is an isometric view of the Respiratory Breathing Filter Apparatus constructed in accordance with and embodying the present invention.

DETAILED DESCRIPTION OF A PREFERRED EMBODIMENT

In the embodiment of the apparatus, as illustrated in FIGS. 1, 2 and 3, there is provided an outer body or housing, which is somewhat arcuate in shape or an "orange-slice" shape to be engaged by the lips and teeth of the user.

By reference to FIGS. 1, 2 and 3, it can be observed that the outer body or housing is arcuately shaped and the center portion of the outer body is bell or dome shaped and resides behind the teeth of the user inward in the mouth, thus conforming more to the natural contours of the user's mouth.

The apparatus is somewhat in the manner of a protective mouthpiece used by boxers and football players. The apparatus cradles the teeth of the user to provide an opening for the teeth of the user to hold the device in position during use. The purpose of this device is to filter the inhaled air, not to protect the teeth of the user.

The outer body or housing has upper and lower wall, which provide recesses 1 and 2, and allows upper and lower rows of teeth to be placed, respectively. In this way, the user can bite down on the outer body or housing and retentively hold the apparatus in position without use of hands. The outer body or housing 3 may be formed of a suitable semi-hard approved plastic or similar material.

The first filter or outer filter extends across the forward arcuate end of the outer body or housing. This filter may be referred to as a macro-particle filter and will remove unwanted large foreign airborne particles from an incoming airstream. This first filter 4 could be of a cloth or fine screen mesh material or the like that can be washed out and reusable.

In FIG. 4, the second filter 5 is spaced apart from the first filter and is located in the interior of the outer body and is removable and is inserted rearwardly of the outer body. The second filter 5 has a concave shape with the hollow cavity internally directed toward the rear of the outer body.

Therefore, said second filter is located inside the user's mouth behind the teeth. The second filter of encased filtering material 6 can be of activated carbon, charcoal or other filtering material. Said filtering material 6 is covered with durable sheer mesh 7 and backing of permeable sterile screen 8 but not limited to said materials, is located inwardly in the path of an incoming airstream, and substantially covers the airway so that small foreign airborne particles may be removed from said incoming airstreams. This filter may be referred to as a micro-particle filter.

Within the hollow cavity of the second filter is an evaporative medicament 9 which is embedded into a permeable sterile screen 10. The medicament 9 is not in contact with the second filter. It is held away and in position as to vaporize into an incoming airstream during inhalation. If the evaporative medicament is not desired, it may be removed easily and replaced with only a permeable sterile screen.

A retaining ring 11 secures the second filter 5 and evaporative medicament 9 on sterile screen 10 in place, preventing any movement of both. The retaining ring fits into a recessed groove 12 in the outer body just rearwardly of the second filter and sterile screen.

Two one-way valves, 13 and 14, are adjacent to the open internal cavity and positioned between the biting surface of the teeth. During inhalation these one-way valves are in the closed position and direct the inhaled airstream through the second filter (5) for small particle filtration. During exhalation, these same one-way valves open to permit the elimination of exhaled air, carbon dioxide and moisture.

The embodiment of the apparatus is unique in that it offers options to air flow and filtration, such as interchanging or removal of component parts. Additionally, an optional prescribed evaporative medicament can be used as needed individually.

It should be understood that many changes, modifications, variations and other uses and applications will become apparent to those skilled in the art after considering this specification and the accompanying drawings. Therefore, any and all such changes, modifications, variations and other uses and applications which do not depart from the spirit and scope of the invention are deemed to be covered by the invention, which is limited only by the following claims.

Having thus described the invention, what I desire to claim and secure by Letter Patent is:

1. A respiratory filter apparatus comprising:
    an arcuate body to be received within a user's mouth;
    said arcuate body having upper and lower grooves to receive the user's teeth for removably holding the body within the mouth of the user;
    means for removing large particles from an inhaled airstream, said means for removing large particles comprising a mesh material or cloth extending across a forward end of the arcuate body adjacent said upper and lower grooves;
    means for preventing increased carbon dioxide levels with the filter apparatus, said means for preventing increased carbon dioxide levels comprising two one-way valves and at least one retaining ring, said one-way valves having a first position during exhalation wherein said one-way valves are open, and a second position during inhalation wherein said one-way valves are closed;
    means for holding an evaporable medicament within said filter apparatus;
    means for removing small particles within an inhaled airstream comprising a concave member spaced behind and apart from said means for removing large particles, said concave member including a loose filtering chemical encased in mesh or screen and further comprising a first layer of mesh, second layer of carbon filtering materials, and a third layer of mesh or screen; said means for holding an evaporable medicament comprising a sterile screen positioned behind and away from said means for removing small particles, a retaining ring and a groove to receive said retaining ring on an interior surface of said arcuate body; and
    means for varying air flow characteristics of an inhaled airstream.

2. The respiratory filter apparatus of claim 1, further comprising means for cooling and moistening inhaled air.

3. The respiratory filter apparatus of claim 2, wherein said means for cooling and moistening inhaled air comprises said means for removing large particles in combination with said evaporable medicament.

* * * * *